United States Patent [19]

Berglund et al.

[11] Patent Number: 4,797,370

[45] Date of Patent: Jan. 10, 1989

[54] ANTIBODY PREPARATION WITH SPECIFICITY FOR 4-(2-AMINOETHYL) IMIDAZOYL GROUP MANUFACTURE AND USE OF THE ANTIBODY PREPARATION

[75] Inventors: Asta B. Berglund; Eva B. Åkerblom, both of Upsala; Anders J. Hedin, Täby, all of Sweden

[73] Assignee: Pharmacia AB, Upsala, Sweden

[21] Appl. No.: 914,825

[22] PCT Filed: Jan. 24, 1986

[86] PCT No.: PCT/SE86/00029

§ 371 Date: Sep. 24, 1986

§ 102(e) Date: Sep. 24, 1986

[87] PCT Pub. No.: WO86/04420

PCT Pub. Date: Jul. 31, 1986

[30] Foreign Application Priority Data

Jan. 24, 1985 [SE] Sweden .................. 8500340

[51] Int. Cl.$^4$ ................ G01N 33/531; G01N 33/532; G01N 33/543; G01N 33/577

[52] U.S. Cl. .................. 436/518; 435/172.2; 435/240.27; 435/948; 436/536; 436/543; 436/547; 436/548; 436/815; 436/822; 530/387; 530/807; 530/808; 935/110

[58] Field of Search .......... 436/518, 529, 536, 543, 436/547, 548, 815, 822; 435/172.2, 240.27, 948; 530/387, 807, 808; 935/110

[56] References Cited

U.S. PATENT DOCUMENTS

| 2,372,066 | 3/1945 | Fell ...................... 530/386 |
| 3,759,890 | 9/1973 | Wilson .................. 530/363 |
| 3,873,697 | 3/1975 | Filipp et al. ............ 424/177 |
| 4,016,146 | 4/1977 | Soares .................... 424/88 |
| 4,122,078 | 10/1978 | Yoshioka et al. ...... 436/815 |

OTHER PUBLICATIONS

Davis et al. Nature (London), 226, 360, 1970.
Hunter, Chem. Abs., 99, 118630c, 1983.
Mita et al., Agents and Actions, 14, 574–579, 1984.
Noller Chemistry of Organic Compounds, 3rd ed., W. B. Saunders Company, Philadelphia, 1965, p. 260.
Panula et al. Proc. Natl. Acad. Sci., U.S.A. 81, 2572–2576 1984.
Roberts et al., Basic Principles of Organic Chemistry W. A. Benjamin, Inc., New York, 1964, p. 1007.
Yoshioka et al., Chem. Abs., 87, 180248q, 1977.
Yoshioka et al., Chem. Abs., 92, 37163F, 1980.

Primary Examiner—Robert J. Warden
Assistant Examiner—David A. Saunders
Attorney, Agent, or Firm—Fred Philpitt

[57] ABSTRACT

Antibody preparation containing antibodies or fragments or derivatives thereof which possess biospecific immunotype affinity to a 4-(2-aminoethyl)imidazolyl group bound to an aliphatic carbon atom; process for manufacturing said preparation; and process for using it.

In said manufacturing process, cells capable of expressing an antibody having a specificity pursuant to the invention are caused in a manner known per se to express said antibody, whereupon said antibody can be isolated and purified in a manner known per se. The antibody preparation of this invention is used as a reactant in immunological assay methods for inter alia histamine and/or histamine determinations.

17 Claims, No Drawings

ANTIBODY PREPARATION WITH SPECIFICITY FOR 4-(2-AMINOETHYL) IMIDAZOYL GROUP MANUFACTURE AND USE OF THE ANTIBODY PREPARATION

The preparation of this invention contains antigen-binding entities i.e. intact antibodies or their antigen-binding fragments or derivatives which are directed against at least one structural element in 4-(2-aminoethyl)imidazolyl. This will thus also imply an antibody activity against histamine and/or against some of the biological degradation products of histamine, in particular 1-methyl-4-(2-aminoethyl)imidazole (=methyl histamine).

When the terms "antibody(ies)" or "antigen binding entity(ies)" are used with reference to the invention, they mean the antibody preparation as such—not the different antigen binding entities that may exist in the preparation.

Very little has been published concerning antibodies possessing specificity for methyl histamine, the reason being presumably that methyl histamine is not considered to be of the same crucial importance biologically as is histamine. Recently however it has been pointed out that quantification of methyl histamine might give potential advantages.

Previously known histamine antibody preparations have all been of poor quality. As a rule their affinity or specificity properties have been inadequate; for example, cross reactivity with other related compounds encountered in vivo has been unacceptably high. One such related compound is histidine which has a natural in vivo concentration more than 1,000 times higher than that of histamine.

U.S. Pat. Nos. 2,301,532, 2,372,066, 3,873,697, Chemical Abstracts 42 (1948) p. 3062-63 (i and a resp.), Agents and Actions 14 (1984) p. 574-79, and Proc. Natl. Acad. Sci. U.S.A. 81 (1984) p. 2572-76 describe the use of various immunogens containing histamine covalently bound to a carrier in essentially two different modes. One of these binding modes utilizes the primary amino group either in an amidated form or directly bound to an azo group. According to the other mode of binding, one position of the histamine imidazole ring is directly bound to an azo, carbonyl or phenyl group. Binding to the primary amino group involves elimination of the structural feature that distinguishes histamine and histidine from each other; such immunogens have been found to be poor in quality. Introduction of an azo, carbonyl or phenyl group on an atom of the imidazole ring involves a major disturbance of the ring electron configuration, which in turn means that the similarity to histamine is largely lost: This perhaps is why such immunogens have never produced antibodies showing any significant degree of specificity for histamine.

Neuroscience Letters 29 (1982) p. 105-06 describes the production of a non-covalent complex of histamine and methylated BSA (bovine serum albumin) and the use of that complex for producing an antiserum to histamine.

U.S. Pat. Nos. 3,759,890 and 4,016,146 ring derivatization of imidazole ring and the benzene ring of phenethylamines are described. None of the products obtained exhibits an aliphatically bound 4-(2-aminoethyl)imidazolyl group.

In a lecture (J. All. Clin. Immunol. 71 (1983) suppl. p. 152) antibodies have been described which are directed against histamine and are said to be exempt from cross reactivity with histidine. They have been employed in an immunological assay procedure.

EP-A No. 110,640 describes a histamine assay method employing histamine receptors from a T-lymphoblastoid cell line.

The antibodies of this invention are to be employed primarily in various immunological assay methods. This however does not in any way exclude the possibility that the antibodies of this invention may also be useful in other fields. Satisfactory immunological assay methods for methyl histamine and/or histamine are quite rare, presumably because no antibody preparations which are good enough for this purpose are available. Histamine determinations have usually been made by employing other techniques, all of which have been cumbersome and time-consuming.

Clinical fields in which histamine determinations have to be made comprise all types of conditions that involve an increased release of histamine, for example in any of the following contexts: For the evaluation of challenges with foodstuffs in cases of suspected foodstuff allergies and eczemas (N. Eng. J. Med. 311 (1984) p. 372-76), for monitoring hyposensitization therapies and symptomatic medication, for the identification of bronchitis versus asthma, and for the identification of allergic rhinitis versus other conditions involving nasal obstruction. It has been suggested that methyl histamine determinations might offer certain advantages.

It will be appreciated from the foregoing that one of the main objects of the present invention reside in providing antibodies possessing specificity for 4-(2-aminoethyl)imidazolyl and low cross reactivity (as compared to previously known antihistamine antibodies) with respect to histidine and with respect to certain types of amines which occur naturally in living organisms and in which the amine function is comprised in a 2-aminoethyl group. Another main object is to provide novel immunological assay methods for 4-(2-aminoethyl)imidazolyl groups, including methods for methyl histamine and/or histamine determinations with high degrees of sensitivity, specificity and precision. A third main object is to provide a process for producing antihistamine antibodies of good and uniform quality, in large amounts, and for prolonged periods of time. Among further objects may be mentioned improvements in the evaluation of histamine assays/determinations within such fields of use as have been recited above.

The antigen-binding entities of this invention are characterized by having biospecific immunotype affinity to an aliphatically bound 4-(2-aminoethyl)imidazolyl group, optionally in a protonated form. Thus these entities possess antibody activity against a 4-(2-aminoethyl)imidazolyl group attached directly as a substituent to an aliphatic carbon atom. The aliphatic carbon atom may be part of a group of formula (i) below, and this group (i) in turn may optionally covalently bind the 4-(2-aminoethyl)imidazolyl group to a carrier (referred to as "histamine carrier" hereinafter). An antibody preparation according to the invention may possess immunotype affinity to histamine and/or the aliphatically bound group (such as in methyl histamine), in which case the diassociation constant should be less than $10^{-8}$ mol/liter (this being equivalent to an affinity constant higher than $10^8$ liter/mol). The affinity (constant) for the aliphatically bound group may range from 10% to up to 2000% of that one for histamine. In case of monoclonals the range may be wider. A substantial part of the histamine binding entities of the preparation are directed towards the aliphatically bound group (with preference for -1-yl or -2-yl). In common practice this means that an immunogen exhibiting the group should be used for the immunization.

Reaction between the antibodies of this invention and histamine and/or methyl histamine is not substantially inhibited by compounds selected from the group consisting of histidine, dopamine and serotonin where. these are present together with the methyl histamine and/or histamine in molar ratios equal to those pertaining to in vivo conditions. In other words: the antibody according to the invention is exempt from cross reactivity with at least one and preferably all of these compounds. This means in actual practice that the inhibition by histidine, calculated for equimolar concentrations relatively to histamine, has to be less than 0.01%, for example less than 0.001%, such as e.g. less than 0.0001%. The corresponding inhibition values for serotonin and dopamine are the following: less than 1%, preferably less than 0.2%, e.g. less than 0.05%. These values apply to the conditions prevailing in Example 15.

In the process for producing antibodies according to the present invention, cells potentially capable of producing such antibodies are caused in a manner known per se to excrete these antibodies which are thereafter isolated and purified in a manner known per se. In a vertebrate (e.g. mammals/including humans/or birds, e.g. fowl) the said excretion may proceed in vivo due to preceding immunization of the vertebrate animal with an immunogen having aliphatically bound 4-(2-aminoethyl)imidazolyl groups. It may be noted here that a specific immune response is obtained due to the fact (as according to expert opinion) that a corresponding antigen has been bound to receptors on B lymphocytes. This will induce the lymphocytes to produce antibodies having the same specificity as the receptors that were utilized in the antigen binding reaction (Essential Immunolgy, Ed Roitt IM; Blackwell Scientific Publications, 4th edition 1983, p. 121-22). It is also possible to raise antibodies by culturing corresponding hybridoma cells in cell cultures in vitro or as ascites tumors. These two latter methods may give antibody preparations which are homogeneous in respect of epitope specificity and affinity.

Purification and isolation may be effected by means of salt precipitation and various chromatographical methods such as e.g. ion exchange, affinity, gel etc. chromatography.

The immunogens as contemplated here are novel compounds characterized by containing a plurality of 4-(2-aminoethyl)imidazolyl groups covalently bound to an immunogenic carrier, in that each such group is bound directly and covalently to an aliphatic carbon atom which preferably forms part of an alkylene chain. The aliphatic carbon atom forms part of a group

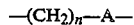  (i)

in which the alkylene (that is, the $(CH_2)_n$ group) is directly attached to the imidazole ring and A is attached directly to the carrier.

In formula (i) above, n is an integer of less than 10, preferably 1 or 2, and A is an inert organic bridge which may for example contain at least one structural element selected from among the following: —NR— (secondary or tertiary amine), —CONR— and —NRCO— (substituted amide), —S—S— (aliphatic disulfide), —S— (aliphatic thioether), —O— (ether), —COO— and —OOC— (ester) and hydrocarbon chain, preferably aliphatic, which may be straight, branched or cyclic and contain from 1 up to 20 carbon atoms, preferably less than 6, as e.g. 1, 2 or 3 carbon atoms. The chain may optionally be substituted by inert functional groups, such as hydroxyl. The symbol R above represents preferably hydrogen but may be alkyl, for instance an alkyl having less than 5 carbon atoms. The term "inert" means that a group or bridge characterized by this adjective is stable in vivo so that the desired immune response can be obtained. The total length of the group (i) will as a rule correspond to that of a chain in which less than 30 atoms are concatenated, preferably less than 20.

The imidazole ring may be attached to the aliphatic carbon atom via the 2- or 5-cabon atom or via the 1- or 3-nitrogen atom. Antibodies possessing optimum specificity for methyl histamine are obtained when the immunogen employed comprises 4-(2-aminoethyl)imidazol-1-yl groups. Antibodies having a higher degree of specificity for histamine than for methyl histamine can be produced if another position of the imidazole ring is bound to the carrier, for instance the 2-position.

The carrier is chosen in accordance with the rules commonly accepted for immunogenic conjugates between a hapten and a carrier. The carrier thus may be water-soluble and high molecular, e.g. an immunogenic protein or polypeptide having a molecular weight within the range of 4,000-10,000 000 dalton, preferably exceeding 15,000 dalton, for instance exceeding 35,000 dalton. Examples of proteins commonly employed are albumins, globulins, enzymes, hemocyanins and the like. Other carriers, too, may be employed if they have a satisfactory degree of immunogenicity; examples are hetero- and homopolymers of amino acids. Carriers may be modified chemically in order to facilitate the introduction of 4-(2-aminoethyl)imidazolyl groups. The number of groups per carrier molecule is chosen within such ranges as will give an intended immunogenic effect. It is not possible to define any exact limits of theses ranges, inasmuch as a humoral immune response is dependent not only on the number of hapten groups but also on the exact type of carrier chosen and on the manner in which the groups are attached (see for instance Progr. Allergy 30 (1982), p. 92–93/Karger, Basel, Switzerland/).

In the light of the knowledge gained up to now the most preferred immunogen for utilization in the present context is one in which the histamine-type group is bound to the carrier via a bridge containing sulfur, preferably a thioether or disulfide structure.

The immunization itself is carried out in a manner known per se, in that the novel immunogen is administered in a manner effective for immunization and in an immunogenically active (effective) amount.

The immune response obtained gives a polyclonal antibody preparation. This means that a desired antibody is present in admixture with other antibodies directed against the immunogen. The said other antibodies comprise species directed against the carrier molecule plus species directed against such structural elements (epitopes) in the 4-(2-aminoethyl)imidazolyl group which are more or less unique for methyl histamine and/or histamine. This means that the specificity in most cases must be narrowed down for obtaining a polyclonal antibody preparation according to the invention. This may potentially be achieved by means of so-called immunosorbent purification, also called IS-purification, although this is a quite cumbersome procedure. Immunosorbent purification comprises removing the specificity for cross reactive substances by means of adsorption, or specifically trapping and then eluting reactive antibodies from the total antibody preparation. A polyclonal antibody preparation is thus treated with such substances in a solid-phase-bound or precipitating form.

The best method of obtaining a good antibody preparation relies on the so-called monoclonal technique. According to this technique, pure cultures of cells are prepared corresponding to the individual clones in a polyclonal antiserum, whereupon the clones producing the desired antibody are selected. First to describe a monoclonal technique have been Kohler and Milstein (Nature 256 (1975) p. 495). This technique implies that a plasma cell derived from immunized mouse spleen and excreting a predetermined antibody is fused with a myeloma cell that is capable of rapid and uninterrupted growth. The spleen cell—myeloma cell hybridoma is established by selective culturing of the cell mixture in hypoxanthine-aminopterinethymidine (HAT) medium. Supernatants of surviving hybrid cell cultures are then assayed for antibody activity against the desired antigen. An aliquot of cells from antibody-producing cultures is cultured and prepared for freezing while another aliquot is employed for cloning of the hybrid cells to form single-cell cultures. In this latter procedure, the cells are cultured at a high degree of dilution for obtaining monoclonal antibodies. Clones excreting the desired antibody are then expanded and several aliquots are frozen while others are employed for large-scale antibody production. The resultant antibodies are then purified and characterized. It should be recalled in this context that a clone will produce antibodies that are specific against only one epitope. By means of culturing the clone corresponding to the desired epitope it is possible to obtain antibody preparations which are homogeneous in respect of their specificity for that particular epitope.

According to one of its aspects the invention relates to a cell capable of producing in vitro an antibody possessing a specificity, affinity and cross reactivity according to this invention. In a preferred embodiment the cell is derived from a fused cell. It is not necessary, according to the invention, that the cell has been brought forth in conformity with the Kohler and Milstein method; on the contrary, any cell producing antibodies with properties according to the invention is comprised within the inventive concept. This aspect thus also covers a cell obtained by means of any future technology, where e.g. specificity in fusion has been still further improved or the immune response has been induced by some means other than immunization.

The antibodies according to the present invention are derivatizable in a manner such as is commonly employed for antibodies. Thus for instance, it is possible to produce in a manner known per se various antigen-binding fragments (e.g. Fab, Fab' and F(ab')2) possessing specificity and selectivity properties analogous to those of the intact antibody. These fragments like the antibody itself may be covalently bound in a known perse manner to various substances such as insoluble or insolubilizable carriers and various analytically detectable groups. Among detectable groups may be noted in particular radioactive, fluorescent, chemiluminescent, enzymatically active etc. groups, including biotinyl groups.

Among various ways of producing derivatives and fragments of the antibodies according to the present invention, mention may be made especially of those which involve splitting of a disulfide bond with concomitant conversion to two reactive disulfide structures (EP-A No. 128,885). Conjugates (antibody conjugates in general) in which these disulfide structures are coupled to solid phases or to analytically detectable groups have been found to retain the original antigen-binding capacity to a very large extent. Moreover good antigen-binding conjugates are also obtained (see for example U.S. Pat. No. 4,232,119) if produced with the aid of heterobifunctional coupling reagents which comprise an amine and/or hydroxyl reactive group together with a thiol reactive group. The term "conjugate" refers to two substances covalently bound together in a manner such that their desired properties are present also in the conjugate.

An immunological assay method according to the invention for detecting or determining 4-(2-aminoethyl-)imidazolyl groups (preferably methyl histamine and/or histamine) is characterized by utilizing an immune reactant selected from among the above-described novel antibodies, fragments thereof and derivatives thereof.

A large number of general types of immunological assay methods are known per se. The artisan who is acquainted with these methods will readily recognize those among them to which the present invention can be applied; and he will also be able to tell in which way this is to be done.

Immunological assay methods utilize immune reactants for forming an immune complex, the formation and amount of which constitute qualitative and quantitative indication means for demonstrating in the sample the presence and amount of an immunological counterpart to an added reactant. To facilitate quantitizing and detection one of the reactants is often added in a labelled form, that is, the reactant is provided with an analytically detectable group. The added amounts of reactants are chosen such that the amount of labelled reactant incorporated in the complex or the amount of labelled reactant remaining free, in a non-complexed state, will be indicative of the amount of the target substance sought.

The immunological methods may be subdivided into for instance "homogeneous" and "heterogeneous" methods. In the case of the homogeneous methods, determination of (assay for) a labelled reactant is carried out without any physical separation of complex-bound labelled reactant from noncomplex-bound reactant. The homogeneous methods use markers which will undergo a change in their activity depending on whether or not they are complex-bound; in this manner it is possible to measure the signal from a reaction mixture containing the marker in both forms, and to draw conclusions from the value obtained as to the amount of the substance looked for. The heterogeneous methods involve physical separation of complex-bound labelled reactant from the non-complex-bound reactant; there is thus no requirement that the marker should undergo any changes in activity. The separation is feasible because one of the two forms of labelled reactant has been or is being bound to a solid phase which is readily separable from the liquid phase. Assays for the analytically detectable group are then carried out on one or both of the two phases.

Also, from another point of view, immunological methods may be subdivided into "competitive" and "non-competitive" methods. In a competitive method the arrangement is such that two reactants having a common epitope are allowed to compete for an insufficient number of homologous binding sites on an immunological counterpart. Usually the systems are chosen such that competition occurs between the substance assayed for and a variant form thereof which is labelled or bound to a solid phase. The amount that binds to the immunological counterpart is a measure of the substance to be detected. In a non-competitive method, the reactants chosen are such that no competition can occur. As examples of non-competitive methods may be mentioned in particular the so-called "sandwich" systems.

According to a third mode of subdivision, the methods comprise precipitation methods on one hand and non-precipitation methods on the other hand. When precipitation methods are carried out the first immune reactions performed will proceed in a homogeneous liquid phase, whereupon the resultant immune complex is precipitated with the aid of a precipitant, e.g. polyethylene glycol, antiserum or solid-phase-bound antibody (care being taken that said antiserum or antibody is not directed against the reactant which is labelled).

A fourth mode of subdivision classifies the methods according to their marker group; thus there are radio-, enzyme-, fluorescence-, chemiluminescence-, enzyme-substrate-immunological etc. methods.

Mixtures of monoclonal antibodies of different specificities and different affinities may provide advantages in immunological assay methods. Thus a finite number thereof such as e.g. 2-5 may be admixed in a single preparation.

In the light of such expert knowledge as has come to the fore up to now the methods preferably employed are competitive systems in a heterogeneous form if the carrier-bound histamine described herein and the antibody of the invention are to be employed in an immunological assay method.

A preferred embodiment of an immunological assay method of this invention employs a conjugate of histamine plus carrier (=histamine carrier). In that conjugate, the 4-(2-aminoethyl)imidazolyl group(s), preferably 1-yl or 2-yl, will be present in an aliphatically bound form.

The histamine carriers that may be employed in the context of this invention bestow new properties on a bound 4-(2-aminoethyl)imidazolyl group. Thus the carrier may have groups or properties that will make a certain particular histamine conjugate analytically detectable, insoluble, or insolubilizable.

Examples of analytically detectable groups are those which are known per se for various immunological assay procedures. As examples of insoluble carriers may be mentioned the various types of hydrophilic particulate or spongy carries employed for such assay procedures, like for instance polyhydroxy- or polyamino-containing polymers such as a polysaccharide in an insoluble form e.g. an insoluble crosslinked dextran derivative, cellulose, starch, agarose etc. Most of the insoluble carriers contemplated here are capable of absorbing water. Examples of insolubilizable carriers are soluble macromolecules of that type which can attach themselves, covalently or by way of adsorption, to various kinds of solid phases such as for instance plastics surfaces.

A 4-(2-aminoethyl)imidazolyl group may be bound to the histamine carrier in the same manner as has been described above for the immunogen. The bond may be established via a group according to formula (i) which is inert, that is, the group is stable and will not substantially diminish the antibody-binding capacity of the 4-(2-aminoethyl)imidazolyl group during practical use. One or more 4-(2-aminoethyl)imidazolyl groups may be bound to one carrier molecule.

That portion of the histamine carrier which forms part of a histamine conjugate has a molecular weight greater than or about equal to that of histamine; that is, its molecular weight will always exceed 100 dalton. This implies for the carrier-bound histamine that its molecular weight always exceeds about 200 dalton.

A carrier-bound histamine to be employed as set forth in the attached claims is produced in that a histamine derivative of the formula (ii)

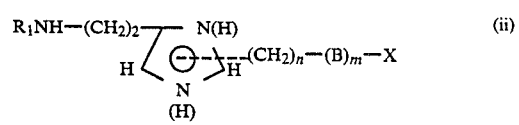

is contacted with a carrier having functional groups Y such that X and Y react so as to form a covalent bond between said derivative and carrier. If $R_1$ is other than hydrogen the group $R_1NH-$ is then converted to a primary amino group $H_2N-$. Throughout this text "(H)" in the formulae means that hydrogen is attached to either one of the two nitrogen atoms of the ring (tautomerism may occur, as is well known), and the broken line ---- indicates that the $(CH_2)_n-(B)_m-X$ is substituted for one of the imidazole hydrogens set forth in formula (ii), preferably in position 1 or 2. In said formula (ii)

n is an integer of less than 10, preferably 1 or 2, m is an integer 0 or 1, and $R_1NH-$ is a group which is chemically inert to X and Y, with $R_1$ being hydrogen or a protective group which is stable under the reaction conditions and is of a type such that after the reaction it can be converted to hydrogen hydrolytically or reductively in a manner that will leave the remaining structures of the resulting compound substantially unaffected.

The protective group is chosen in accordance with known principles (see for example Protective Groups in Organic Synthesis; Greene TN; John Wiley & Sons Inc.; U.S.A. 1981, in particular p. 218-87 and the Tables on p. 323-34). Factors to be taken into account when the group is chosen are inter alia the stability of the carrier, the reactivity of X and Y, and the type of structure formed upon reaction of X and Y. Protective groups commonly employed are such that will form carbamates with the amino group ($H_2N-$); for example, $R_1 = (CH_3)_3Si(CH_2)_2OOC-$ and $(CH_3)_3COOC-$ (both of which are stable in alkaline media).

In formula (ii) X and Y are functional groups chosen such that they can be made to react with each other chemically so as to form a covalent structure binding the derivative (ii) and the carrier together. X and Y may be the same or different and may be selected from among electrophilic and nucleophilic groups. If they are a pair of electrophilic groups or a pair of nucleophilic groups it is possible for instance to (a) employ oxidative coupling for forming the bond (e.g. $-SH + -HS- \rightarrow -S-S-$) or (b) react one of the groups of the pair chemically to form a group of the opposite type that will not react with $R_1NH-$. An example of this latter case is activation with bifunctional coupling reagents (also called activation reagents). These are well known to persons skilled in the art. If X is nucleophilic and Y electrophilic or vice versa these two groups can usually be reacted with each other without any preceding activation.

Examples of reactive electrophilic groups are activated carboxyl, for example carboxylic acid halide, mixed carboxylic acid anhydride, N-succinimidyl carboxylate; activated hydroxyl, for example halocyanoactivated hydroxyl, alkyl halide, preferably alpha-iodinated alkyl carbonyl ($CH_2X_1-CO-$, $X_1$=iodine) etc; activated amine, for example halocyanoactivated amine; activated thiol, preferably so-called aliphatically bound reactive disulfide (—S—S—R') where R' is defined as being such that a compound R'SH is thermodynamically stabilized as compared to —S—S—R'; and carbon-carbon double bond, preferably conjugated with carbonyl, nitro or cyano. Examples of electrophilic groups are those that possess a free electron pair on a sulfur, nitrogen or oxygen atom, such as (a) —SH, for example aromatic and aliphatic thiol and corresponding anions, (b) —NHR, for example primary and secondary amines where R is selected from among hydrogen, lower alkyl and aryl, and (c) —OH, for example alcohol, phenol and carboxylic acid or their corresponding anions. By selecting a suitable combination of electrophilic and nucleophilic groups as X and Y a man skilled in the art will easily find his way in forming an ester, a substituted amide, an ether, a thioether or a secondary or tertiary amine in the reaction for coupling derivative (ii) to a desired carrier.

An important nucleophilic group is a primary amine ($H_2N-$) which is present in derivative (ii) if $R_1=H$. This means that if one of X and Y is a nucleophil and the other of X and Y is an electrophil which is reactive both with primary amines and with said nucleophil then it is imperative that $R_1$ is a protective group, in order to avoid coupling at $R_1NH-$. The necessity of introducing a protective group usually makes work with many electrophilic and nucleophilic groups rather cumbersome. Such a protective group can be avoided if a so-called soft electrophil and soft nucleophil are chosen as X and Y respectively, or vice versa. Soft electrophils are carbon-carbon double bonds, aliphatically bound reactive disulfides and alpha-halogenated alkyl carbonyl groups, preferably iodinated groups, e.g. ($ICH_2-CO-$). Among soft nucleophils may be mentioned HS— (thiol) as the foremost representative. In the most preferred method for binding histamine to a carrier soft electrophils and soft nucleophils are employed. This applies particularly to carriers which are sensitive to hydrolysis.

In formula (ii) the group B may be an organic bridge of a length of less than 14 atoms. Group B has to be inert in the sense that it must not contain any structure that would significantly disturb the intended interaction between 4-(2-aminoethyl)imidazolyl and the desired histamine receptor (for instance antibody). Group B may contain structural elements selected from among the same as for A above.

In the reaction, group A in formula (i) is formed. It thus contains the bridge B according to formula (ii), the bridge via which Y may be attached to the carrier, and the bridge that has been obtained by the reaction of X with Y.

In synthesis contexts, reactive disulfides (—S—S—R') are well known to persons skilled in the art (see Europ. pat. appln. Nos. 82850071.0, 82850072.8 and 84850153.2, EP-A-30,490 and others). R' is defined as being such that when —S—S—R' is reacted with HS— this will cause R'—SH to be released and stabilized thermodynamically so as to remain excluded from participation in any further thiol-disulfide exchange reactions. Many thiol compounds (R'SH) fulfill this condition due to the fact that in aqueous solutions they will spontaneously tautomerize into their thione forms (HR"=S); or in other words, their thione forms are more stable than the corresponding thiol forms. A prerequisite for this may be that the sulfur atom of the thiol group is bound to a carbon atom in a heterocyclic aromatic ring in a manner such that the sulfur atom is at a distance from a ring heteroatom extending over an uneven number of atoms.

Among examples of R' whose thiol compounds when subjected to the reaction will spontaneously stabilize due to formation of the corresponding thione forms by way of tautomerism or resonance, the following may be mentioned: 5-nitro-pyridyl, 5-carboxy-2-pyridyl, 2-pyridyl, 4-pyridyl, 2-benzothiazolyl, 4-nitro-3-carboxyphenyl, and the N-oxides of the aforesaid pyridyl groups.

Compounds having the structure (ii) may be produced in various ways. Some of the compounds are already known (see for example GB-A No. 1,341,375, (1,4-bis-(2-aminoethyl)imidazole trihydrochloride and 1-carboxymethyl-4-(2-aminoethyl)imidazole dihydrochloride) and DE-A No. 3,322,117, and after suitable derivatization these can contain other functional groups (X), bridges (B) and/or protective groups ($R_1$).

A route of synthesis that has been developed in the context of the present invention will be described below in general terms.

In this synthesis, histamine is reacted in a first step with an acylating reagent by which the 1-N and alpha-N atoms of histamine are each converted into a carbamate structure (—OCONH—) such that the carbamate on the 1-N atom can afterwards be split off selectively. Examples of suitable acylating reagents are 2-(trimethylsilyl)ethyl chloroformate, di-tert.butyl dicarbonate and other reagents that will form carbamates of comparable hydrolytic and/or reductive stability. The two reagents specifically mentioned will give the protective groups $(CH_3)_3Si(CH_2)_2OOC-$ and $(CH_3)_3COOC-$, respectively. Acylation is usually carried out in an anhydrous medium, desirably so in aprotic liquids in which histamine and the other reagents are soluble; but it is also possible to carry out the acylation in protic solvents in which the acylating reagent employed reacts preferentially with histamine without at the same time being subject to any substantial solvolysis. When the protective group on the 1-N atom is to be split off this can be done in protic solvents, e.g. aqueous media, under the action of a tertiary amine such as for instance triethylamine. The two protective groups specifically mentioned above have been found to be very suitable for a large number of applications. Due to their stability they can be split off selectively which is a necessary prerequisite for the second step of the synthesis. They moreover permit the splitting to be performed under mild conditions at the alpha-N atom after further steps of the synthesis have been carried out (note for instance that the carriers employed are in many cases quite sensitive to hydrolysis). Protective groups for amines and the way in which they may be chosen, introduced and removed have been described in the aforesaid book "Protective Groups in Organic Chemistry". —The product obtained in this first step has the formula

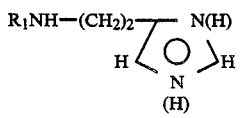

in which $R_1$ is a protective group introduced with the aid of the aforesaid acylating reagents.

Compound (iii) is then reacted with an alkylating reagent, for example formaldehyde together with a primary lower alkylamine (Mannich reaction) or with only 2-haloethylamine, preferably 2-bromoethylamine, so that an alkylation introducing an aminoalkyl group takes place on the imidazole ring. What is obtained is usually a mixture of different monoalkylated isomers of structure (ii) where n is 1 or 2 (depending on the alkylating agent employed), m is 0, $R_1$ is the protective group introduced earlier and X is a primary or secondary amine. The isolated isomer mixture or alternatively each isomer separately may be attached to a carrier as has been indicated earlier. In cases where the alkylation is performed with 2-bromoethylamine it has been found that the reaction conditions may be chosen such that the imidazole ring can be alkylated in position 1 with high yields.

The alkylation conditions are such as are previously known for each respective reagent, but it may be mentioned here that it is advantageous to perform the reaction in aprotic solvents in the presence of potassium hydroxide when 2-haloethylamine is employed.

The compound thus obtained can then be reacted with a carrier having the general formula

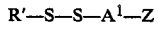

to form carrier-bound histamine of the general formula

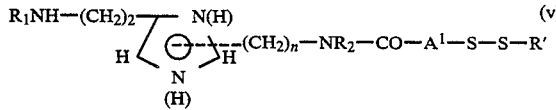

whereupon if required $R_1$ may be converted to hydrogen in that the protective group is split off.

In formulae (iv) and (v), the symbols $R_1$, (H) and ---- have the same meanings as above, n is 1 or 2, $R_2$ may be hydrogen or lower alkyl of less than 5 carbon atoms, R'—S—S is a reactive disulfide, $A^1$ is for example a straight, branched or cyclic hydrocarbon chain, preferably aliphatic, which comprises more than 1 and less than 8 carbon atoms, preferably less than 5, and Z is an activated carboxyl group (e.g. N-succinimidyl carboxylate, or analogous compounds as according to U.S. Pat. No. 4,199,003, acid halide, mixed anhydride and carbodiimide).

The invention will now be further illustrated by means of a number of non-limitative working examples. These examples provide very good evidence that the histamine antibodies of this invention are quite different from those that have been known heretofore and for this reason will presumably be of paramount importance for histamine determination procedures.

The examples mention the names of Sephadex ®, Sepharose ®, and Phadezyme ®. These are commercial names of products from Pharmacia AB, Sweden.

I. Preparation of 4-(2-aminoethyl)imidazolyl bound to various carriers

Structural formulae are set forth on separate pages.

EXAMPLE 1

Preparation of 1-(N-(3-(2-pyridyldithio)propionyl)-2-aminoethyl)-4-(2-aminoethyl)imidazole trihydrochloride (V)

1. A. Preparation of 2-(trimethylsilyl)ethylchloroformate 43.6 ml of 12.5% phosgene in toluene is poured into a reaction flask and cooled to $-40°$ C. Then 3.5 ml (24 mmol) of 2-trimethylsilylethanol is added dropwise at $-35°$ C. The temperature of the reaction solution is allowed to rise slowly overnight to ambient. Excess phosgene is distilled off in vacuo. The trimethylsilyl chloroformate in toluene thus obtained is used as such in the next step of the synthesis, without preceding purification.

1. B. 4-(N-(2-trimethylsilylethyloxycarbonyl)-2-aminoethyl)imidazole (I)

1.84 g (10 mmol) of histamine dihydrochloride is slurried in 50 ml of methylene chloride, and 6.2 ml (44 mmol) of triethylamine is added. The thus resultant mixture is added portionwise to 2-trimethylsilylethylchloroformate in toluene (prepared as described above) at 10°–15° C. The reaction mixture is stirred at room temperature overnight. Undissolved material is filtered off and identified by NMR as being triethylamine hydrochloride. The toluene solution is evaporated, the residue then being slurried in 30 ml of ethyl acetate. 1.0 g of undissolved triethylamine hydrochloride is removed by filtration. The ethyl acetate solution is evaporated, and the residue is slurried twice in petroleum ether. The petroleum ether solutions are evaporated and 1.0 g of a semicrystalline product is obtained; by NMR analysis this product is identified as being histamine in which both the amino group and ring nitrogen have been acylated with 2-trimethylsilylethylchloroformate. The acyl group on the ring nitrogen is removed by treatment of the product for 2 hours with 100 μl of triethylamine in 50 ml of methanol. The solution is evaporated to leave an oil which is transformed into white crystals by treatment with 30 ml of ether. More precipitate is obtained upon addition of 75 ml petroleum ether. 560 mg of I is obtained upon filtration. The structure of the product is established with the aid of its NMR spectrum. $^1$H NMR spectrum (CDCl$_3$) expressed as values: 2H 7.60 s, 5H 6.82 s, —NH— 5.20, —C$\underline{H}_2$CH$_2$—O— 4.15 t, —OCONHC$\underline{H}_2$— 3.50 m, 4-C$\underline{H}_2$-imidazole 2.82 t, SiC$\underline{H}_2$CH$_2$ 1.00 t, (C$\underline{H}_3$)$_3$Si 0.03 s.

1. C. 1-(2-aminoethyl)-4-(N-(2-trimethylsilylethyloxycarbonyl)-2-aminoethyl)imidazole (II) and 3-(2-aminoethyl)-4-(N-(2-trimethylsilylethyloxycarbonyl)-2-aminoethyl)imidazole (III)

294 mg (1.15 mmol) of I, 1,180 mg (5.75 mmol) of 2-bromoethylamine hydrobromide, 700 mg (10.75 mmol) of 86% potassium hydroxide and 40 ml of acetonitrile are introduced into a 100 ml round-bottommed flask and stirred for 44 hours at room temperature. After that period of stirring a greyish white precipitate has been formed on the walls of the flask. The acetonitrile solution is filtered and evaporated, the residue then being dissolved in 12 ml of water. The aqueous solution has a pH of 8.5. The solution is extracted with 3×12 ml of ethyl acetate. The ethyl acetate solutions are pooled, dried with MgSO₄, filtered and evaporated. 240 mg of a solid product is obtained. According to its NMR spectrum the product is a mixture of 60% II, 10% III and 30% starting material (I). NMR spectrum (CDCl₃) of II, expressed as values: 2H 7.43 s, 5H 6.75 s, —CH₂C-H₂O 4.13 t, 1—CH₂-imidazole 3.96, —CONHCH₂— 3.48 m, —CH₂NH₂ 3.03 t, 4-CH₂-imidazole 2.72 t, SiCH₂CH₂ 1.98 t, (CH₃)₃Si 0.02 s. NMR of compound III: 2H 7.51 s, 5H 6.85 s, CHhd 2CH₂—O 4.13 t, 3-CH₂-imidazole about 3.96, CONHCH₂ 3.48 m, —CH₂NH₂ 2.87 t, 4-CH₂-imidazole about 2.66 t, —SiCH₂CH₂ 0.98 t, (CH₃)₃Si 0.02 s. Products I, II and III are separable by HPLC.

1. D.
1-(N-(3-(2-pyridyldithio)propionyl)-2-aminoethyl)-4-(N-(2-trimethylsilylethyloxycarbonyl)-2-aminoethyl)imidazole (IV)

96 mg (0.32 mmol) of II is dissolved in 2.4 ml of methylene chloride. Next follows an addition of 45 μl of triethylamine and 99.8 mg (0.31 mmol) of N-succinimidyl-3-(2-pyridyldithio)propionate (SPDP, Pharmacia AB, Sweden) dissolved in 1.7 ml of methylene chloride. The reaction mixture is stirred at room temperature for a period of 45 minutes. Water-soluble substances are removed by washing, this being carried out by means of stirring with 2×5 ml phosphate buffer, pH 7, for 1 hour. The methylene chloride phase is dried over MgSO₄ and evaporated. The residue is washed with petroleum ether overnight. Undissolved substance is HPLC purified on a μ-Bondapak C18 column (Prep.) with methanol-water 75:25 as the mobile phase. The sample is divided into five runs. The desired fractions are pooled, the methanol is distilled off in vacuo, and an oil precipiaates. This oil is extracted into methylene chloride. After drying over MgSO₄ the solution is evaporated. 52 mg of IV are obtained. NMR spectrum (CDCl₃): 6H-pyridine 8.2, 4H-pyridine 7.6, 3H- and 5H-pyridine about 7.1–7.2, 2H-imidazole 7.4, 5H-imidazole 6.76, CH₂CH₂O 4.11 t, 1-CH₂-imidazole 4.07 t, —CH₂NHCO 3.61 m, OCONHCH₂ 3.45 m, —CH₂S— 3.08 t, 4-CH₂-imidazole 2.72 t, COCH₂— 2.61, —SiCH₂— 0.97 t, (CH₃)₃Si 0.08 s.

1. E.
1-(N-(3-(2-pyridyldithio)propionyl)-2-aminoethyl)-4-(2-aminoethyl)imidazole trihydrochloride (V)

13 mg (0.026 mmol) of IV is dissolved in 1 ml of acetonitrile containing 0.15 ml of conc. HCl. The reaction mixture is stirred at room temperature for 2.5 hours. TLC on silica gel with EtOAc—MeOH—NH₄OH (80:20:1) as the mobile phase shows that the trimethylsilylethyloxycarbonyl protective group has been completely removed after 2.5 hours. The reaction solution is evaporated, whereupon an NMR analysis is run in D₂⊖+ deuterated acetonitrile.

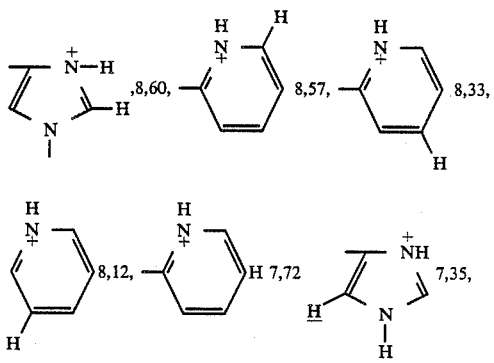

1-CH₂-imidazole 4.18 t, —CH₂NHCO 3.52 t, H₃N+CH₂— 3.18 t, 4-CH₂-imidazole about 3.0 t, —CH₂S— 3.0 t, —COCH₂— 2.57 t.

EXAMPLE 2

Alternative synthesis of 1-(N-(3-(2-pyridyldithio)propionyl)-2-aminoethyl)-4-(2-aminoethyl)imidazole trihydrochloride (V)

2. A.
4-(N-(tert-butyloxycarbonyl)-2-aminoethyl)imidazole (VI)

75 ml of acetonitrile, 1.84 g (10 mmol) of histamine dihydrochloride, and 7 ml (50 mmol) of triethylamine are mixed in a 100 ml round-bottomed flask, whereupon 6.56 g (30 mmol) of di-tert-butyl dicarbonate is added. The reaction mixture is stirred at room temperature for 19 hours and then filtered. The acetonitrile solution is evaporated, and the residue is washed with 50 ml of petroleum ether. Undissolved substance is treated with 2×100 ml of ether. The ether phases are pooled and evaporated. A crystalline product is obtained which is identified by NMR to be histamine having both its amino group and its ring nitrogen acylated with tert-butyloxycarbonyl. The acyl group on the ring nitrogen is removed by treatment of the product with 400 μl of triethylamine in 50 ml of methanol for 3.5 days. The solution is evaporated to thus leave an oil, the latter then being dissolved in 20 ml of ether. 40 ml of petroleum ether is added to the ether solution; this results in precipitation of an oil which crystallizes on stirring. 1.13 g of product VI is obtained the structure of which is established by NMR analysis, the NMR spectrum (CDCl₃) being the following: 2H 7.58 s, 5H 6.82 s, —CONHCH₂— 3.41, 4-CH₂-imidazole 2.81 t, (CH₃)₃C 1.43 s.

2. B.
1-(2-aminoethyl)-4-(N-(tert.butyloxycarbonyl)-2-aminoethyl)imidazole (VII)

2.15 g (33.9 mmol) of 88% KOH are weighed out and introduced into a 100 ml round-bottomed flask. This is followed by additions of 60 ml acetonitrile and 650 mg (3.1 mmol) of compound VI and then finally 3.14 g (15.4 mmol) of 2-bromoethylamine hydrobromide. The reaction mixture is stirred for 20 hours at room temperature. TLC in EtOAc—MeOH—NH₄OH (80:20:1) shows that all of VI has reacted. The reaction mixture is filtered and the precipitate is washed with 2×25 ml of acetonitrile. The acetonitrile solutions are pooled and evaporated. The evaporation residue is dissolved in 35 ml of water. The aqueous solution thus obtained has a pH of 11; this is adjusted to pH 7.5 with 5M HCl, whereupon the solution is extracted with 4×15 ml of ethyl acetate in order to remove residual unreacted VI. Next the aqueous phase is saturated with sodium chloride and extracted with 4×20 ml of acetonitrile. The acetonitrile solutions are pooled, dried with $MgSO_4$ and evaporated, the resultant evaporation residue being an oil, 320 mg. The product can be identified by NMR as being the hydrochloride salt of VII. It is difficult to obtain a satisfactory degree of resolution in the NMR analysis of this hydrochloride salt, and for this reason the free base has been prepared by dissolving the product in water, adjusting the pH to 10.4 and then extracting VII into methylene chloride. NMR ($CDCl_3$): 2H 7.43 s, 5H 6.74 s, 1-$CH_2$-imidazole 3.96 t, —CONHC-$\underline{H_2}$— 3.42 m, $CH_2NH_2$ 3.04 t, 4-$CH_2$-imidazole 2.74 t, $(CH_3)_3C$ 1.45.

2. C.

1-(N-(3-(2-pyridyldithio)propionyl)-2-aminoethyl)-4-(N-(tert-butyloxycarbonyl)-2-aminoethyl)imidazole (VIII)

300 mg (1.18 mmol) of compound VII in its hydrochloride form is dissolved in 7.5 ml of methylene chloride and introduced into a 50 ml round-bottomed flask. Next 165 μl (1.18 mmol) of triethylamine is added followed by 368 mg (1.18 mmol) of N-succinimidyl-3-(2-pyridyldithio)propionate (SPDP reagent, Pharmacia AB) dissolved in 5 ml of methylene chloride. The reaction solution is stirred for 1 hour at room temperature and is then left to stand in a refrigerator for 1 hour. Water-soluble substances are removed by shaking of the methylene chloride solution with 4×20 ml of phosphate buffer pH 7.0. The methylene chloride solution is dried with $MgSO_4$ and evaporated. The residue is dissolved in ethyl acetate. The ethyl acetate solution is shaken with 2×15 ml phosphate buffer pH 7.5. The ethyl acetate solution is dried with $MgSO_4$ and evaporated. The residue is dissolved in methylene chloride and shaken with a further 3×20 ml of phosphate buffer pH 7.0. The methylene chloride solution is dried with $MgSO_4$ and evaporated, which gives 321 mg of product. By means of NMR analysis this product is identified as being compound VIII. The NMR spectrum ($CDCl_3$) is the following: 6H-pyridine 8.23, 4H-pyridine 7.60 m, 3- and 5H-pyridine about 7.1 m, 2H-imidazole 7.37 s, 5H-imidazole 6.74 s, 1-$CH_2$-imidazole 4.07 t, —$CH_2$NHCO— 3.58 m, OCO—NH$CH_2$ 3.38 m, —$CH_2$S— 3.08 t, 4-$CH_2$-imidazole 2.69 t, —CO$CH_2$— 2.63 t, $(CH_3)_3C$ 1.42 s.

2. D.

1-(N-(3-(2-pyridyldithio)propionyl)-2-aminoethyl)-4-(2-aminoethyl)imidazole trihydrochloride (V)

2 mg (4.5 μmol) of VIII is dissolved in 0.2 ml of aceonitrile. 20 μl of conc. HCl is added, whereupon the solution is allowed to stand at room temperature. According to TLC in EtOAc—MeOH—$NH_4OH$ (80:20:1) the protective group, tert-butyloxycarbonyl, has been split off by hydrolysis after 45 minutes. The solution is evaporated, and the product obtained is identified by NMR as being compound V.

EXAMPLE 3

4-(N-(2-trimethylsilylethyloxycarbonyl)-2-aminoethyl)imidazole substituted in its position 1, 2, 3 or 5 with propylaminomethyl (compounds X, XI, XII, XIII respectively)

82 μl (1 mmol) of n-propylamine is dissolved in 5 ml of 0.4M phosphate buffer pH 5.8 in a reaction vessel. Next are added 120 μl (1.5 mmol) of 37% formaldehyde and 127.5 mg (0.5 mmol) of compound I dissolved in 3.5 ml of ethanol. The reaction mixture is stirred at room temperature for 5 days. Then the solution obtained is evaporated, the residue being dissolved in 20 ml of ethyl acetate. The ethyl acetate solution is shaken with 3×10 ml saturated $Na_2CO_3$ solution and then dried with $MgSO_4$ and evaporated. The reaction product is identified by means of NMR as being a mixture of several products. The predominant product is compound X; in addition compounds XI, XII and XIII are present in amounts that can be isolated. Also disubstituted products are detectable. The isomers can be coupled to carriers via the secondary amine group.

EXAMPLE 4

Preparation of 4-(2-aminoethyl)imidazolyl albumin (product XIV)

4. A. Iodoacetylated dog albumin 284 mg of dog albumin (0.25 mmol lysine) is dissolved in 100 ml of 0.05M borate buffer pH 8.1 at 0° C. Thereafter 42.9 mg (0.15 mmol) of N-succinimidyl iodoacetate is added, and the reaction solution is stirred for 4 hours on an ice bath. Undissolved material is removed by filtration. The solution is transferred to a Sephadex®) G-25 column K50/60 and eluted with 0.9% NaCl. The protein fraction is collected (144 ml) and concentrated in an Amicon cell through a PM10 filter to a volume of 19.6 ml, whereupon it is frozen. The protein content is determined by means of amino acid analysis. 10.8 mg of protein per ml is obtained. Gel filtration of iodoacetylated dog albumin reveals the molecular distribution to be the same as in the dog albumin starting material. A minor portion is desalted through a PM10 filter and lyophilized. The product is analyzed in respect of its protein content and iodine, and is found to contain 81.4% protein and 2.4% I. Degree of modification: 16 iodoacetyl groups per albumin.

4. B.

1-(N-(3-thiopropionyl)-2-aminoethyl)-4-(2-aminoethyl)imidazole (IX).

Direct coupling of compound IX to iodoacetylated dog albumin (Product XIV)

Preparation of compound IX 0.5 ml of 0.1M boric acid buffer pH 8 is added to 0.0067 mmol of compound V in 0.25 ml of acetonitrile containing 38 μl of conc. HCl. The pH is adjusted to 8 at first with solid $NaHCO_3$ and then finally with some drops of saturated $NaHCO_3$ solution. The reaction vessel is flushed with gaseous nitrogen. Next 25.4 mg (0.67 mmol) of sodium borohydride is added. The pH rises to 9.4 and is adjusted to pH 8 by means of 2M HCl. The reaction solution is stirred at room temperature for 30 minutes under gaseous nitrogen. The amount of 2-thiopyridone that has formed is checked by UV analysis in order to make sure that disulfide bond reduction has been complete. Excess $NaBH_4$ is destroyed by acidification of the reaction solution with 5M HCl to pH 3. The solution is left standing for 1 hour at room temperature, whereupon its pH is adjusted to 7.5 with solid NaHCO$_3$.

Preparation of product XIV

The aforesaid solution is added dropwise to 32.3 mg of iodoacetylated dog albumin in 1.2 ml of water. The total volume of the reaction solution is then 2.3 ml. The solution is stirred for 1 hour at room temperature, the stirring then being followed by desalting on a Sephadex ® G-25 PD10 column with water as the eluent. 4.5 ml of protein fraction is collected. A portion of the solution is lyophilized and analyzed for S and protein content; the values obtained are S 1.9% and protein 67%. Degree of modification: twenty-seven 4-(2-aminoethyl)imidazolyl groups per albumin molecule. This high degree of modification suggests that compound (IX) may also have coupled to disulfide groups naturally occurring in the albumin.

EXAMPLE 5

Preparation of 4-(2-aminoethyl)imidazolyl-beta-galactosidase (Product XV)

Coupling of compound (V) to reduced beta-galactosidase (XV)

A freshly prepared solution of 1.05 μmol of compound V in 500 μl of 0.2M borate buffer, pH 8.0, containing 2 mM MgCl$_2$, is added to 7 mg of reduced beta-galactosidase (which contains about 15 free SH groups) dissolved in 2 ml of 0.2M borate buffer, pH 8.0, containing 2 mM of MgCl$_2$. The reaction solution is left to stand at first for 1 hour at room temperature and then during the night in a refrigerator. The reaction is monitored by UV measurement of the amount of thiopyridone formed. After 1 hour all the 15 free SH groups have reacted with compound V. The reaction solution is purified on a Sephadex ® G-25 PD10 column. The eluent employed is an 0.1M phosphate buffer, pH 7.4, containing 0.1M NaCl, 2 mM MgCl$_2$ and 0.05% NaN$_3$. A 3.3 ml protein fraction is collected.

EXAMPLE 6

Preparation of crosslinked insoluble dextran (Sephadex ®) having 4-(2-aminoethyl)imidazolyl groups (product XVI).

Coupling of compound V to thiopropyl-Sephadex ® G-50 beads (product XVI)

6.6 mg (13.4 μmol) of compound IV is hydrolyzed for 2.5 hours in 0.5 ml of acetonitrile containing 76 μl of conc. HCl, to thus form compound V. The pH of the reaction solution is raised to 7.2 by addition of 500 μl of 0.1M phosphate buffer and solid NaHCO$_3$. Gaseous nitrogen is bubbled through the solution. Then the solution is added to a slurry of 100 mg of thiopropyl Sephadex ® G-50 containing 11.4 μmol of SH groups in 0.1M phosphate buffer pH 7.2. The mixture is agitated in a rotary mixer for 20 hours at room temperature. The gel is transferred to a Pasteur pipette. The reaction mother liquor is allowed to drain off, and the gel is washed with 6×1.5 ml of 0.05M phosphate buffer pH 7.4. The amount of thiopyridone that has formed is UV-analyzed in the reaction mother liquor+wash liquors. An amount of 4.45 μmol thiopyridone is detected, indicating that 4.45 μmol of compound V has been coupled to 100 mg of dry beads.

EXAMPLE 7

Preparation of 4-(2-aminoethyl)imidazolyl agarose (0.5–5μ)

Coupling of compound V to agarose beads with an

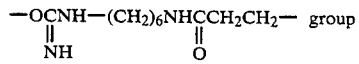

as the coupling link (product XVII)

7. A. Preparation of aminohexyl agarose beads 2 g of lyophilized CNBr-activated micro agarose beads (according to Example 10 and U.S. Pat. No. 3,645,852) are swelled for 15 min. in 1 mM HCl, whereupon they are carefully washed seven times on a glass filter with 1 mM HCl. After the last suction the gel is slurried in 6 ml of 1M hexamethylenediamine solution, pH 11, containing 1M NaCl. This mixture is agitated on a shaker for 45 minutes and then filtered through a glass filter. The gel is washed alternately with 0.1M acetate buffer, pH 4.0, containing 1M NaCl, and 0.1M hydrogen carbonate buffer, pH 8.3, containing 1M NaCl, four times each. The last washing is performed with hydrogen carbonate buffer.

Next the gel is slurried in 35 ml of 0.1M ethanolamine having an HCl-adjusted pH of 8 and containing 1M NaCl. The mixture is stored in a refrigerator overnight. The gel is suction drained and washed 6 times with 0.1M phosphate buffer, pH 7.5, containing 0.1M NaCl. The gel is allowed to settle in a measuring cylinder overnight and then drained by suction on a glass filter. 1.2 g of moist gel is obtained.

This gel is slurried in 5.5 ml of 0.1M phosphate buffer, pH 7.5, containing 0.1M NaCl and 2 ml ethanol. To this slurry are added 6.2 mg (20 μmol) of N-succinimidyl-3-(2-pyridyldithio)propionate dissolved in 2 ml of ethanol, and the mixture is agitated on a shaker for 30 min. at room temperature. This is followed by washing with 0.1M phosphate buffer, pH 6.5, containing 0.1M NaCl. The mixture is centrifuged and the wash liquor is sucked off. The washing procedure is repeated four times.

Thereafter the gel is slurried in 4 ml of phosphate buffer, pH 6.5, containing 0.1M NaCl. To this mixture are added 3.2 mg (20 μmol) of dithioerythritol dissolved in 1 ml phosphate buffer, pH 6.5, containing 0.1M NaCl. The mixture is agitated on a shaker for 1 hour at room temperature. This is followed by addition of 15 ml of phosphate buffer. pH 6.5, containing 0.1M NaCl; the mixture is then centrifuged. The solution is separated, and the gel is washed 4 times with phosphate buffer, pH 6.5, containing 0.1M NaCl and then finally with phosphate buffer pH 7.5 containing 0.1M NaCl.

The reaction mother liquor and the first wash liquor are pooled for being UV analyzed in respect of the amount of thiopyridone formed in the reaction. The result of this analysis indicates that the gel contains 8.2 μmol of SH groups per g of suction-drained gel.

B. Coupling of compound V to agarose beads (product XVII)

The above gel is slurried directly in 2.5 ml of phosphate buffer pH 7.5—0.1M NaCl. To this is added a solution of 10 μmol of compound V in 1 ml of 0.1M phosphate buffer, pH 7.5, containing 0.1M NaCl. The mixture is agitated on a shaker for 1 hour at room temperature, whereupon it is diluted with 15 ml buffer and centrifuged. The gel is washed 6 times with 0.1M phosphate buffer, pH 7.5, containin 0.1M NaCl, and finally with 0.1M phosphate buffer, pH 7.0, containing 0.1M NaCl and 0.03% NaN$_3$.

The reaction mother liquor and the first wash buffer solution are subjected to UV analysis with respect to their content of thiopyridone compound as formed in the reaction. The result of this analysis indicates that the gel is substituted with 2.9 μmol of 4-(2-aminoethyl-)imidazolyl groups per g of suction-drained gel.

EXAMPLE 8

Preparation of 4-(2-aminoethyl)imidazolyl agarose (product XVIII).

Coupling of compound V to Sepharose ® 6MB beads with an

as the coupling link (product XVIII)

The procedure is analogous to the synthesis of product XVIII according to the preceding example, with the exception that the particles of agarose material employed are larger (so-called "macrobeads", Sepharose ® 6MB).

By using the direct histamine assay (J Clin Immunol 1 (1981) p 73–9) it has been shown that the beads (product XVIII) do in fact retain lymphocytes by virtue of their histamine receptors. This property has further been confirmed by showing that the non-adherent population of the cells is no longer able to make significant amounts of histamine suppressor factor (HSF). Examples 4, 5, 6, 7 and 8 make use of the fact that pyridyl disulfide groups are demonstrable analytically.

EXAMPLE 9

Preparation of radioactively labelled histamine (product XX)

9. A.

1-(N-(3-(4-hydroxyphenyl)propionyl)-2-aminoethyl)-4-(2-aminoethyl)imidazole (XIX)

The following materials are introduced into a reaction vessel: 5 mg (0.02 mmol) of compound VII dissolved in 0.5 ml methylene chloride; 2.8 μl (0.02 mmol) of triethylamine; and last 5.3 mg (0.02 mmol) of N-succinimidyl-3-(4-hydroxyphenyl)propionate dissolved in 0.5 ml of methylene chloride. The solution is stirred for 2 hours at room temperature and then evaporated. The residue is dissolved in 0.5 ml of trifluoroacetic acid, and hydrolysis is allowed to proceed for 1 hour and 15 minutes at room temperature. The solution is evaporated, the residue then being separated on a reversed-phase column PepRPC (Pharmacia AB) with an 0.1% trifluoroacetic acid - acetonitrile gradient. At about 7% acetonitrile compound XIX is eluted. The structure has been confirmed by NMR analysis, the NMR data being the following: 2H-imidazole 8.3, 5H-imidazole 7.2, O-H-hydroxyphenyl 7.1, m-H-hydroxyphenyl 6.85, 1-CH$_2$-imidazole 4.15, —CH$_2$NHCO 3.55, —CH$_2$N$^+$H$_3$ 3.25 t, 4-CH$_2$-imidazole 3.05 t, p-CH$_2$-hydroxyphenyl 2.75 t, —CH$_2$CO 2.5 t.

9. B.

1-(N-(3-(4-hydroxy-3-iodo/$^{125}$I/phenyl)propionyl)-2-aminoethyl)-4-(2-aminoethyl)imidazole (XX)

6.62 nmol of XIX in 13.8 μl ethanol, 2.16 μl of Na$^{125}$I (13.8 MBq/μl) and 50 μl of Chloramine-T solution (10 μl of 0.2M chloramine-T + 3,000 μl of 0.2M phosphate buffer pH 7.0) are mixed and allowed to react for 1 minute. Next 10 μl of 0.1M sodium thiosulfate is added and then finally, after 1 minute, 200 μl of 0.1% trifluoroacetic acid. The solution is purified with FPLC on a PepRPC column (Pharmacia Fine Chemicals).

EXAMPLE 10

Preparation of 4-(2-aminoethyl)imidazolyl agarose with short bridge (product XXII)

Coupling of compound VII to agarose beads (0.5–5μ) (product XXI). Hydrolysis of XXI to XXII 2 g of lyophilized CNBr-activated agarose beads (0.5–5μ) are made to swell and are washed in 1 mM HCl (total about 250 ml). (Activation process according to U.S. Pat. No. 3,645,852). The moist gel obtained upon gentle suction weighs 1.3 g. It is mixed with 2 mg (7.8 μmol) of compound VII dissolved in 0.5 ml of ethanol and 4 ml of 0.1M hydrogen carbonate buffer, pH 8.3, containing 0.5M NaCl. The mixture is agitated on a shaker for 2 hours at room temperature and then subjected to centrifugation. The beads are washed once with coupling buffer and once with 0.1M acetate buffer, pH 4.0, containing 0.5M NaCl.

CNBr-activated groups that have not reacted with VII are blocked by shaking for 2 hours at room temperature in 10 ml of 1M ethanolamine in 0.5M NaCl, pH 8.2. The mixture is then centrifuged and washed alternately with coupling buffer and acetate buffer as above (three times with each buffer).

The resultant product XXI is hydrolyzed to XXII; this is done in 5 ml of 0.5M HCl for 3 hours at room temperature. The beads are then washed alternately with coupling buffer and acetate buffer as above.

Confirmation that XXII contains coupled histamine without tert-butoxycarbonyl group was obtained with the aid of monoclonal mouse IgG directed specifically against aliphatically bound 4-(2-aminoethyl)imidazolyl.

EXAMPLE 10-1

Preparation of 4-(2-aminoethyl)imidazolyl avidine

Coupling of compound V to avidine with —COCH$_2$CH$_2$S— as the coupling link 10-1. A. Preparation of 3-mercaptopropionyl avidine 2.5 mg (1.35 μmol lysine) of avidine is dissolved in 2 ml of 0.1M phosphate buffer, pH 7.5, containing 0.1M NaCl. 0.21 mg (0.68 μmol) N-succinimidyl-3-(2-pyridyldithio)propionate dissolved in 40 μl ethanol is added, and the solution so obtained is stirred at 8° C. for 1.5 hours. Substances of low molecular weight are removed from the solution on a PD 10 column (Sephadex ® G 25M, Pharmacia AB, Uppsala, Sweden), 0.1M acetate buffer, pH 4.5, containing 0.1M NaCl being used as eluent. The high molecular weight avidine fraction, 3.5 ml, is collected and concentrated to 1.5 ml on a YM 10 ultrafilter (Amicon).

15 mg of dithioerythritol is dissolved in 0.5 ml of acetate buffer as above and added to the concentrated avidine fraction. The solution is stirred for 20 minutes at room temperature and the so obtained 3-mercaptopropionyl avidine is purified from low molecular contaminants on a PD 10 column, 0.1M phosphate buffer, pH 7.5, containing 0.1M NaCl being used as eluent.

10-1. B. Coupling of compound V to 3-mercaptopropionyl avidine 0.98 μmol of compound V dissolved in 0.25 ml aqua distillata with pH adjusted to 8.0 by NaHCO₃, is added to the 3-mercaptopropionyl avidine solution from example 10-1 A. The reaction mixture is stirred at room temperature for 1 hour, whereupon it is concentrated to 2 ml through a YM 10 ultrafilter (Amicon). The so produced 4-(2-aminoethyl)imidazolyl avidine is purified on a PD 10 column as in example 10-1 A. 0.1M phosphate buffer, pH 7.5, containing 0.1M NaCl being used as eluent. The formation of thiopyridone is measured spectrophotometrically at 343 nm and the avidine concentration can be measured at 280 nm. From the data so obtained a substitution degree of 3 mol histamine per mol avidine can be calculated.

Formulae of compounds synthesized:

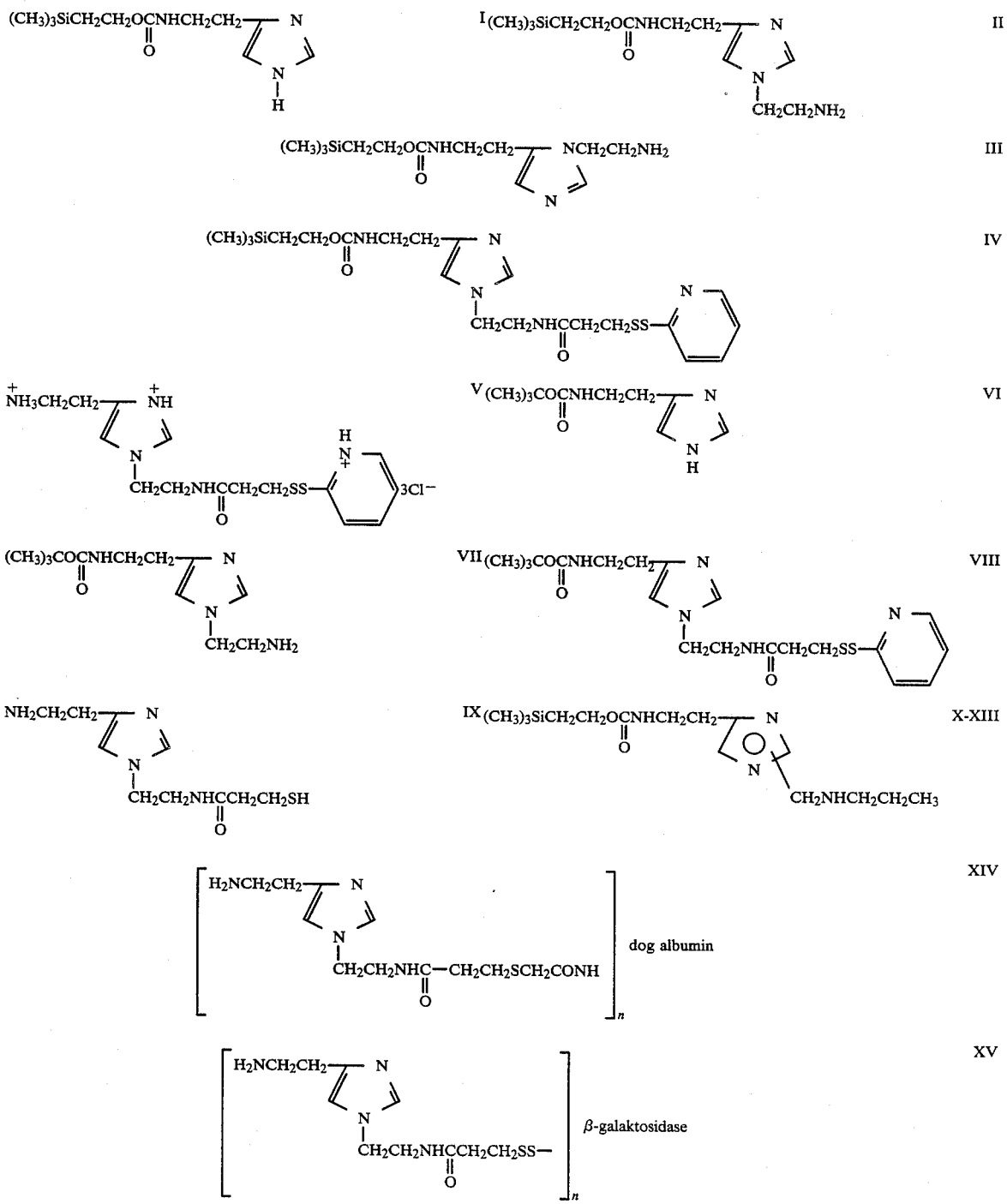

-continued

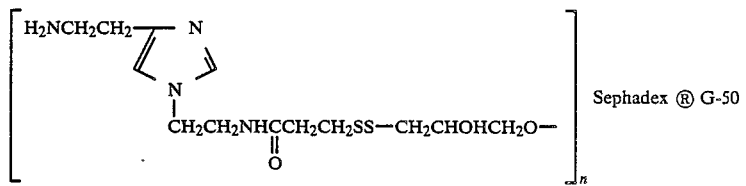
XVI

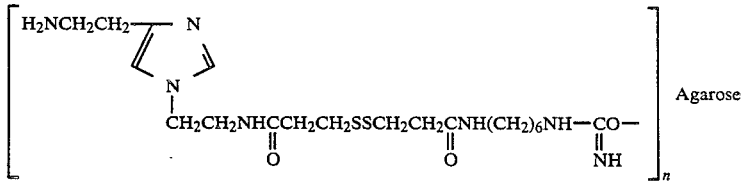
XVII

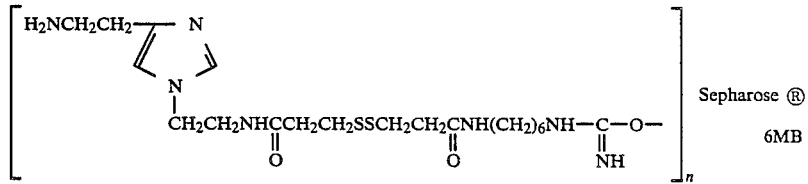
XVIII

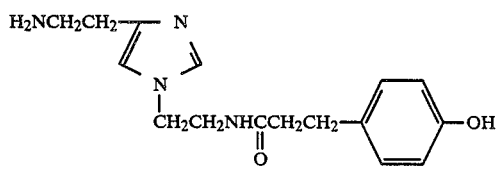
XIX

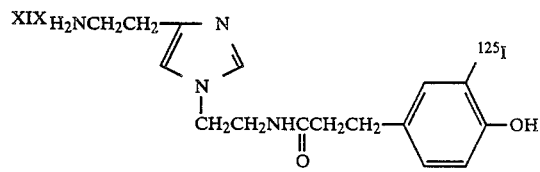
XX

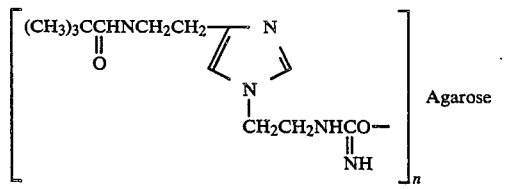
XXI

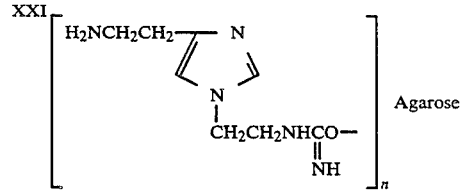
XXII

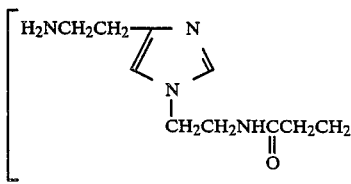

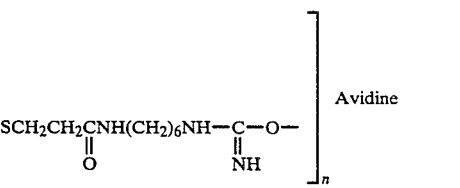
XXIII

II. Production of antibody preparations

EXAMPLE 11

Production of monoclonal antibodies

Antibodies to histamine were produced by hybridization of mouse myeloma cells with spleen cells from mice immunized with 1-(N-(3-thiopropionyl)-2-aminoethyl)-4-(2-aminoethyl)imidazole dog serum albumin conjugate (XIV, from Example 4). The hybridization step and the subsequent culturing and cloning of the hybrids were carried out as described in Research Monographs in Immunology Vol. 3, General Editor I. L. Turk, Elsevier/North Holland, Biomedical Press New York 1981.

In short, Balb/c Dub mice (Flow Laboratories, Dublin, Va., U.S.A.) were immunized by subcutaneous and intraperitoneal injections of 75 μg purified immunogen emulsified in Freund's complete adjuvant. 50 μg of immunogen (XIV) (from Example 4) was administered intraperitoneally after four weeks on 3 consecutive days. Then 3 days after the last booster injection the spleens were taken from the mice for hybridization.

The myeloma cells employed in this hybridization step were cells of myeloma cell line Sp 2/0 (Nature 276, 269 (1978)). $10^8$ spleen cells were mixed with $1-3\times 10^7$ myeloma cells in Dulbecco's medium (from Flow Laboratories, Inglewood, Calif., U.S.A.). Cells were centrifuged down and all of the supernatant was removed. 1 ml of 50% (w/v) polyethylene glycol (mw 4,000) was added slowly to the cells, with gentle stirring. After 1-2 minutes the cell suspension was diluted slowly with 5 ml of Dulbecco's medium. The cells were centrifuged down, washed and divided into 300-500 cell cultures (wells) in 0.2 ml of Dulbecco's medium containing 15% (w/v) of fetal calf serum, 20 μg/ml gentamicin sulfate, L-glutamine 2 mM, sodium pyruvate 1 mM, hepes buffer 10 mM and 2-mercaptoethanol $10^{-5}$M. The plates incubated at +37° C. in air with 7% $CO_2$. Half of the culture medium in each well was replaced by fresh medium containing hypoxanthine-aminopterine-thymidine (HAT, $10^{-4}$M hypoxanthine, $4\times10^{-7}$M aminopterine and $1.6\times10^{-5}$M thymidine) on days 1, 4 and so forth every three days for 2 weeks. After this, HT medium for 1 week. The cell cultures were examined in respect of their specificity for histamine and methyl histamine (1-methyl-4-(2-aminoethyl)imidazole), this examination being carried out by means of an immunosorbent method using an enzyme marker, ELISA (Eva Engvall and Peter Perlmann, J. Immunol. 109, p. 129-135, 1972). The positive cultures discovered by means of this method were cloned repeatedly in accordance with the so-called "limiting dilution" method (Oi and Herzenberg, 1980) and were then propagated in cell culture.

The cells were cultured serum-free in Iscoves' medium (Gibco Europe) with addition of 10 $\mu$/ml transferrin, 10 $\mu$/ml insulin, 20 $\mu$M ethanolamine, 2 mM glutamine and $1\times10^{-5}$M 2-mercaptoethanol. The antibodies were purified on a cation exchanger (SP-Sephadex ® C 50) and finally fractionated on Superose ® 6B (Pharmacia AB). The final antibody concentration was 10 mg/ml).

EXAMPLE 12

Method for enzyme-immunological determination of histamine and methyl histamine, employing antibodies possessing specificity for these two compounds.

12. A. Coupling of rabbit-antimouse-IgG antibodies to CNBr-activated agarose Agarose beads (0.5-5$\mu$, Pharmacia AB) are CNBr-activated (according to Example 10 and U.S. Pat. No. 3,645,852) and subjected to suction on a glass filter funnel. 8 g of this activated gel is mixed with 4 mg of rabbit-antimouse antibodies in 36 ml of 0.1M $NaHCO_3$ and incubated on a shaker overnight at +4° C. Thereafter, the reaction mixture is centrifuged for 10 minutes at 2,000×g, the supernatant then being removed by suction. Next follows washing with 40 ml of 0.1M Tris buffer+1M NaCl, pH 8.1, for 10 minutes, then centrifugation and suction. Incubation with 40 ml acetate buffer+1M NaCl, pH 4.0, for 10 minutes, centrifugation and suction. Incubation with 40 ml of 1M ethanolamine-HCl, pH 9.0 for 1 hour, centrifugation and suction. The aforesaid washings with Tris buffer and acetate buffer are repeated twice. 40 ml of 0.05M phosphate buffer+1M NaCl+0.01M EDTA+0.05% Tween 20 are added and incubated for 10 minutes. This is followed by centrifugation and suction. Washing with said phosphate buffer is repeated twice. the gel is diluted to 0.3 g/ml in phosphate buffer and is then sonicated.

12 B. Determination of Histamine

Analysis was carried out in Ellerman tubes. To all the tubes was added 0.1 ml of enzyme-labelled histamine (from Example 5) diluted 140 000 times in 0.05M phosphate buffer with 0.9% (w/v) NaCl and 0.3% (W/v) human serum albumin, 0.05% (w/v) $NaN_3$ and 2 mM $MgCl_2$ (pH 7.4).

0.1 ml of standard solutions containing 1,000,250, 62.5, 15.6, 3.9, 0.98, 0.24, 0.061 $\mu$g/l histamine diphosphate was added to tubes Nos. 1 to 8. 0.1 ml of phosphate-buffered saline was added to one tube.

To all the tubes was added an 0.1 ml portion of diluted monoclonal antibodies (from Example 11, possessing specificity for histamine), the dilution being $10^6$ in phosphate-buffered saline containing 2 mM $MgCl_2$. The mixture was incubated overnight at room temperature.

1 ml of the diluted gel (Example 12 A) was added and incubated on a shaker for 1 hour at room temperature. The tubes were washed 3 times with 0.9% by weight of NaCl aqueous solution containing 0.05% by volume of Tween 20. The last washing step was followed by decantation.

0.2 ml of o-nitrophenyl galactoside substrate in 0.2M phosphate buffer (Phadezyme ® substrate) was incubated for 2.5 hours at +37° C. The reaction was terminated by addition of 1 ml $NaHCO_3$ (4.24 g/100 ml of water). The color developed was read off spectrophotometrically at 420 nm; the results thus obtained were the following:

| Histamine concentration, $\mu$g/l | Absorbance at 420 nm |
| --- | --- |
| 1 000 | 0.04 |
| 250 | 0.115 |
| 62.5 | 0.255 |
| 15.6 | 0.344 |
| 3.9 | 0.380 |
| 0.98 | 0.394 |
| 0.24 | 0.405 |
| 0.061 | 0.405 |
| $B_o$ = phosphate buffer | 0.400 |

On the basis of the absorbance values obtained and corresponding values of an unknown sample the histamine content of the sample can be estimated.

12. C. Determination of methyl histamine (1-methyl-4-(2-aminoethyl)imidazole)

Antibodies employed were methyl histamine specific antibodies from Example 11 and solid phase bound rabbit-antimouse-IgG antibodies from Example 12 A. Incubations were carried out in accordance with Example 12 B. The results obtained were the following:

| Methyl histamine, $\mu$g/l | Absorbance at 420 nm |
| --- | --- |
| 1 000 | 0.004 |
| 250 | 0.008 |
| 62.5 | 0.014 |
| 15.6 | 0.050 |
| 3.9 | 0.139 |
| 0.98 | 0.269 |
| 0.24 | 0.364 |
| 0.061 | 0.390 |
| $B_o$ = phosphate buffer | 0.400 |

On this basis it is then possible to estimate the content of methyl histamine in an unknown sample, in a manner analogous to Example 12 B.

Example 13

Radioimmunological method for determination of methyl histamine. Competitive method

13. A. Preparation of agarose beads with covalently bound antibodies specific for histamine and methyl histamine Antibodies produced according to Example 11 are coupled to CNBr-activated agarose (0.5-5$\mu$) by the method described in Example 12 A.

13. B. Determination of methyl histamine
(1-methyl-4-(2-aminoethyl)imidazole)

0.1 ml of agarose-bound antibodies (1 mg/ml, from Example 13 A) in phosphate-buffered saline, pH 7.4, is added to 10 Ellerman tubes.

0.1 ml of the sample to be examined is added to one of the tubes (tube No. 10). 0.1 ml of the methyl histamine standard solution containing 1,000, 250, 62.5, 15.6, 3.9, 0.98, 0.24 and 0.06 µg/l is added to tubes Nos. 1-8 respectively; buffer alone is added to tube No. 9.

0.1 ml of iodine-labelled histamine from Example 9 (XX) is added to each tube.

Incubation on a shaker proceeds at room temperature overnight, whereafter the agarose particles are centrifuged and washed 3 times with 0.9% by weight of sodium chloride. The tubes are then finally transferred to a gamma counter. The counts per unit time for standard samples are calculated as % of the $B_o$ sample and inserted in a lin log diagram from which it is possible to calculate the amount of methyl histamine present in the unknown test sample.

| Methyl histamine, µg/l | Counts per minute |
|---|---|
| 1 000 | 212 |
| 100 | 173 |
| 25 | 260 |
| 6.25 | 453 |
| 1.50 | 966 |
| 0.39 | 1 345 |
| 0.098 | 1 605 |
| 0.024 | 1 861 |
| $B_o$ | 1 966 |

EXAMPLE 14

Radioimmunological method for determination of histamine. Competitive method

14. A. Production of $^{125}$I-labelled antibody

Monoclonal antibodies produced according to Example 11 are labelled with $^{125}$I in conformity with the method described by Hunter and Greenwood (Nature Vol. 194, 1962, p. 495).

14. B. Determination of histamine 0.1 ml of histamine diphosphate standard solution containing 100 µg/l is added to one tube; phosphate-buffered saline alone is added to a second tube.

0.1 ml of gel (XVII) from Example 7 is added to each tube.

0.1 ml of $^{125}$I-labelled antibodies from Example 14 A (30 ng/ml) is then added to each tube, whereupon the mixtures are incubated overnight at rest at room temperature. Three washings with 0.3M NaCl, 0.1% Tween 20. The tubes are counted in a gamma counter.

| Histamine, µg/l | cpm |
|---|---|
| 100 | 1 047 |
| $B_o$ = phosphate buffer | 2 379 |

On the basis of these values and corresponding values of an unknown sample a rough estimate of the amount of histamine in the sample can be obtained.

EXAMPLE 15

Cross reactivity studies

Cross reactivity of an antibody according to Example 11 has been tested against histidine, serotonin and dopamine. The study was carried out in the same manner as in Example 12, but with the putative cross reactant substances tested as standard samples, the uptake then being compared to that obtained with histamine.

| Histamine concentration, µg/l | Absorbance at 420 nm |
|---|---|
| 1 000 | 0.012 |
| 6.25 | 0.286 |
| 0.098 | 0.353 |

| Histidine | Absorbance at 420 nm |
|---|---|
| 1 mg/ml | 0.423 |
| 100 µg/ml | 0.436 |
| 0.1 ng/ml | 0.448 |

Cross reactivity with histidine was not detectable, that is, was clearly below 0.001% at equimolar concentrations.

| Serotonin | Absorbance at 420 nm |
|---|---|
| 1 mg/ml | 0.058 |
| 100 µg/ml | 0.225 |
| 0.1 ng/ml | 0.390 |

Cross reactivity with serotonin was 0.025% calculated for equimolar concentrations.

| Dopamine | Absorbance at 420 nm |
|---|---|
| 1 mg/ml | 0.06 |
| 0.01 mg/ml | 0.267 |
| 10 ng/ml | 0.352 |
| 1 ng/ml | 0.330 |

Cross reactivity with dopamine was 0.1% calculated for equimolar concentrations.

The antibody tested cross reacted with histamine and methyl. histamine, with a preference for methyl histamine (about 5-15 times).

EXAMPLE 16

Polyclonal antibodies (antiserum)

16. A. Production of polyclonal antibodies 1-(N-(3-thiopropionyl)-2-aminoethyl)-4-(2-aminoethyl)imidazole dog serum albumin conjugate (XIV) from Example 4 is injected intramuscularly in rabbits (French ram), 3×0.2 mg protein per animal, at 14 days' intervals. This was followed by booster injections, 0.1 mg per animal, 1 g per month. The first three injections were performed with Freund's complete adjuvant and subsequent injections with Freund's incomplete adjuvant. Bleedings were made 1-2 weeks after the injections, beginning after 7-8 weeks of immunization. The antiserum obtained was adsorbed with solid-phase-bound dog serum albumin.

16. B. Coating of microplates having 96 wells 1-(N-(3-thiopropionyl)-2-aminoethyl)-4-(2-aminoethyl)imidazole dog serum albumin conjugate (from Example 4) is diluted in 0.1M sodium carbonate buffer pH 9.5 to a concentration of 2.5 µg/ml. The wells in untreated microtiter plates of polystyrene were coated with 200 µl of the diluted antigen overnight at room temperature. The plates were then stored in a refrigerator at +4° C. Before use, the plates are washed three times with 0.9% weight of aqueous NaCl containing 0.05% by volume of Tween ® 20.

16. C. Production of enzyme-labelled antirabbit antibodies 0.3 ml of alkaline phosphatase (5 mg/ml) Type VII from Sigma and 0.1 ml of IS-purified sheep-antirabbit antibody suspension containing 5 mg/ml in phosphate-buffered saline are dialyzed at +4° C. overnight. 2.5% (w/v) glutaraldehyde is added to a final concentration of 0.2% glutaraldehyde. The solution is incubated 2-3 hours at room temperature, and the mixture is dialyzed once more against phosphate-buffered saline overnight at +4° C. 0.05% of $NaN_3$ is added and, optionally, a protective protein.

16. D. Determination of antibody activity against aliphatically bound 4-(2-aminoethyl)imidazolyl Analyses were carried out in wells of microtiter plates coated as decribed in 16 B above. 200 µl of the antibody solution diluted 10, 100, 1,000 and 10,000 times in phosphate-buffered saline with 0.05% Tween 20 is added to the wells which are then incubated for 2 hours at +37° C. Next follow three washings with 0.9% by weight of sodium chloride containing 0.05% by volume of Tween ® 20. To each well is then added a 200 µl portion of enzyme conjugate solution, from 16 C, diluted 1,000 times in phosphate-buffered saline containing 0.05% by volume of Tween ® 20. Incubation 2 hours at +37° C. The plate is washed three times as above, followed by addition of 200 µl of substrate p-nitrophenyl phosphate (1 mg/ml) diluted in 1M diethanolamine-HCl, 1 mM $MgCl_2$ pH 9.8. The plate is then incubated in the dark for 15-30 minutes at room temperature. The color developed is read off spectrophotometrically at 410 nm.

| Antibody dilution | Absorbance at 420 nm |
| --- | --- |
| 1/10 | 0.790 |
| 1/100 | 0.613 |
| 1/1000 | 0.256 |
| 1/10000 | 0.082 |

16. E. Determination of polyclonal antibody activity against histamine and methylhistamine.

Polyclonal antibodies were produced. (Example 16 A). Microtiter plates were coated with histamine and methylhistamine as in Example 16 B. 200 µl/well (concentration 2.5 µg/ml). Enzyme-labelled antirabbit antibodies were produced as in Example 16 C.

Analyses were carried out as in 16 D above.

| Antibody dilution | Absorbance at 420 nm |
| --- | --- |
| Histamine | |
| 1/1 000 | 1.69 |
| 1/10 000 | 0.77 |
| 1/100 000 | 0.10 |
| 1/1 000 000 | 0.008 |
| Methylhistamine | |
| 1/1 000 | 1.55 |
| 1/10 000 | 0.71 |
| 1/100 000 | 0.106 |
| 1/1 000 000 | 0.001 |

The affinity of the antibodies was found to be similar for histamine and methylhistamine.

Examples 15 and 16 E show that the affinity (constants) for histamine in relation to an aliphatically bound 4-(2-aminoethyl)imidazolyl group may vary within wide ranges. (40%-2,000%)

EXAMPLE 17

Affinity constants of monoclonal antibodies

Preliminary experiments for the estimation of the affinity constant between one of the monoclonal antibodies and its immunogen have indicated a high value.

The invention is defined in the attached claims which form an integral part of this specification.

We claim:

1. An anti-histamine antibody preparation in which a substantial part of the anitgen-binding entities that possess immunological affinity for histamine also possess immunological affinity for an aliphatically bound 4-(2-aminoethyl)imidazolyl group.

2. An anti-histamine antibody preparation according to claim 1 in which all the antigen-binding entities that possess immunological affinity for histamine also possess immunological affinity for the 4-(2-aminoethyl)imidazolyl group.

3. An anti-histamine antibody preparation according to claim 2, in which the antigen-binding entities possessing immunological affinity for histamine are a mixture of different monoclonal antibodies.

4. An anti-histamine antibody preparation according to claim 2 which is monoclonal.

5. In an immunological assay method for the determination or detection of 4-(2-aminoethyl)imidazolyl groups, the improvement comprising employing as one of the immune reactants an anti-histamine antibody preparation according to claim 1.

6. An immunological assay method according to claim 5 wherein the antibody preparation contains less than five different monoclonal anti-histamine antibodies possessing immunological affinity to an aliphatically bound 4-(2-aminoethyl)imidazolyl group.

7. An immunological assay method according to claim 6 wherein the antibody preparation contains one monoclonal antibody of the said immunological affinity.

8. An immunological assay method according to claim 7 which is heterogenous.

9. An immunological assay method according to claim 7 wherein one of the immune reactants employed consists of a histamine conjugate exhibiting at least one aliphatically bound 4-(2-aminoethyl)imidazolyl group.

10. An immunological assay method according to claim 9 wherein said conjugate exhibits at least one anlytically detectable group that is bound to said at least one aliphatically bound 4-(2-aminoethyl)imidazolyl group.

11. A method according to claim 9 wherein said conjugate is insoluble or insolubilizable in aqueous media.

12. A process for the preparation of an anti-histamine antibody preparation comprising exposing cells potentially capable of producing anti-histamine antibodies to aliphatically bound 4-(2-aminoethyl)imidazolyl groups conjugated to an immunogenic carrier, thereby causing said cells to excrete antibodies, whereupon the excreted antibodies are isolated and purified.

13. A process according to claim 12 wherein the antibodies are fragmented after isolation.

14. A process according to claim 12 wherein the antibodies are derivatized after isolation.

15. A process according to claim 12 in which the cells are caused to excrete the antibodies by an immunization in vivo.

16. A process according to claim 12 in which the cells are spleen-myeloma hybrid cells which are cultured in order to excrete the antibodies.

17. An anti-histamine antibody preparation having an affinity constant for aliphatically bound 4-(2-aminoethyl)imidazolyl within the range of from 10% to 2,000% of its affinity constant for histamine.

* * * * *